United States Patent [19]

Kesling, Jr. et al.

[11] Patent Number: 4,594,185
[45] Date of Patent: Jun. 10, 1986

[54] ALKOXYLATED PLASTICIZER ALCOHOL ETHER SULFATE SURFACTANTS

[75] Inventors: Haven S. Kesling, Jr., Drexel Hill; Hyman D. Gillman, Spring City, both of Pa.

[73] Assignee: Atlantic Richfield Company, Los Angeles, Calif.

[21] Appl. No.: 624,322

[22] Filed: Jun. 25, 1984

[51] Int. Cl.$^4$ .................. C11D 1/14; C07C 141/02
[52] U.S. Cl. .................... 252/551; 252/532; 252/545; 252/DIG. 14; 558/34
[58] Field of Search ............. 252/526, 532, 545, 551; 260/458 R

[56] References Cited

U.S. PATENT DOCUMENTS

| | | | |
|---|---|---|---|
| 3,775,349 | 11/1973 | Tuvell et al. | 252/551 |
| 3,843,706 | 10/1974 | Weil et al. | 252/551 |
| 3,875,202 | 4/1975 | Steckler | 260/458 |
| 3,931,271 | 1/1976 | Baumann et al. | 260/458 |
| 3,956,401 | 5/1976 | Scardera et al. | 252/170 X |
| 4,077,917 | 3/1978 | Panzer | 252/545 |
| 4,259,215 | 3/1981 | Murata et al. | 252/528 |
| 4,395,364 | 7/1984 | Murata et al. | 252/526 |

FOREIGN PATENT DOCUMENTS 2226988 12/1973 Fed. Rep. of Germany .
84399 6/1980 Japan .
738538 10/1955 United Kingdom .
797119 6/1958 United Kingdom .

OTHER PUBLICATIONS

T. P. Matson, *Soap and Chemical Specialties*, Nov. 1963.
J. Clebicki et al., *Synthesis and Surface Activity of Sodium Polyoxypropylated Higher Alcohol Sulfates, Tenside Detergents*, 17 130–134 (1980).

*Primary Examiner*—Prince E. Willis
*Attorney, Agent, or Firm*—Michael S. Jarosz

[57] ABSTRACT

Alkoxylated ether sulfate anionic surfactants of this invention are prepared by conventional procedures, e.g., oxyalkylation with propylene oxide or 1,2-butylene oxide of a straight chain plasticizer range alcohol; optionally followed by oxyalkylation with ethylene oxide or with a mixture of ethylene oxide and higher alkylene oxide; sulfation of the alkoxylated product; and neutralization of the sulfated derivative. The alkoxylated ether sulfate anionic surfactants of the present invention are liquids which exhibit superior detergency to polyester fabrics, excellent hard water stability, organic solubility, low foaming, low odor, and exhibit excellent compatibility with non-ionic and other surfactants in detergent formulations.

14 Claims, No Drawings

ALKOXYLATED PLASTICIZER ALCOHOL ETHER SULFATE SURFACTANTS

BACKGROUND OF THE INVENTION

1. Field of the Invention

This invention relates to the production of certain novel alkoxylated ether sulfate anionic surfactants based on plasticizer range linear alcohols. More particularly, this invention relates to certain novel relatively short chain ether alcohol sulfate anionic surfactants from propylene oxide or 1,2-butylene oxide, which exhibit properties comparable to or better than commercial surfactants prepared from "detergent" range alcohols.

2. Description of the Prior Art

During the last several years, primary "detergent" range alcohol ethoxylated sulfates have been used extensively in large volume surfactant applications such as light duty liquid dishwashing detergents, concentrated laundry detergents, hard surface cleaners, and as textile surfactants. The advantages of the ethoxylated ether sulfates over the previously employed alcohol sulfates include ready synthesis, increased solubility, and insensitivity to hard water (see for example T. P. Matson, Soap and Chemical Specialties, November 1963).

Propoxylated and butoxylated alcohol ether sulfate anionic surfactants have been disclosed in the prior art, but are not known to have been employed in commercial applications. A substantial portion of prior art disclosing such surfactant compositions deals only with "detergent" or fatty range alcohols, i.e. $C_{12}-C_{18}$ alcohols, as disclosed, for example, in Weil et al. U.S. Pat. No. 4,383,706, and with short oxypropylene chains generally containing between about 1 and 3 propylene oxide units, as disclosed, for example in Tuvell et al U.S. Pat. No. 3,775,349. Although certain ether alcohol sulfate compositions derived from straight chain carbon alcohols of shorter chain length and containing greater than 3 oxypropylene units have been studied, for example, by J. Chlebicki et al, *Synthesis and Surface Activity of Sodium Polyoxypropylated Higher Alcohol Sulfates*", Tenside Detergents, 17, 130–134 (1980), the authors conclude that these materials are generally inferior surfactants as compared with propoxylated surfactants prepared from "detergent" range alcohols.

Fabric softeners employable in the laundry wash, rinse or dryer cycle are desired for commercial application. Furthermore, because of the inconvenience of rinse and dryer cycle application, the industry is attempting to develop softeners that are compatible with wash cycle applications. Cation quaternary ammonium salts, which are used commercially in fabric softening applications, cannot be used in the wash cycle with anionic surfactants. It is believed that the cationic and the anionic materials complex and precipitate, thus reducing detergency. Although wash cycle detergent-/fabric softner formulations have been prepared from non-ionic surfactants and cationic softners, these formulations lack the detergent power that can be obtained when an anionic surfactant is used as the detergent.

Accordingly, it is an object of this invention to provide new and useful anionic surfactants based on plasticizer range linear alcohols, i.e. relatively short chain, as compared with detergent alcohols.

A further object of the present invention is to provide water and organic solvent soluble anionic surfactant compositions characterized as being low foaming and free of unpleasant odor, and which exhibit excellent detergency, particularly with respect to use of polyester fabrics and excellent stability in hard water.

It is another object of this invention to provide non-viscous, readily flowable, liquid, highly active concentrated anionic surfactant composition requiring no added solubilizing agent.

Other objects of this invention are readily apparent to those skilled in the art from the following description.

DESCRIPTION OF THE INVENTION

The anionic surfactant compositions of the present invention correspond to the formula:

$$RO-[Ch_2CH(R')O]_m Z_n SO_3 M \quad \text{(Formula I)}$$

wherein R is a primary hydrocarbon alkyl radical containing of from about 4 to 10 carbon atoms; R' is a member selected from the group consisting of methyl and ethyl; m is an integer of from 7 to 12, preferably 8 to 10; Z is an oxyethylene group or a random mixture of oxyethylene groups and oxyalkylene groups present in the radical $[CH_2CDH(R')O]$, the molar ratio of oxyethylene to oxyalkylene groups in said mixture being such that the total molar ratio of oxyethylene to oxyalkylene groups in said formula is from about 1:1 to 1:10; n is an integer of from 0 to 4; and M is hydrogen, an alkali metal, an alkaline earth metal; ammonium or a primary, secondary, tertiary or quaternary alkyl ammonium or alkylolammonium ion.

Illustrative alkoxylated ether sulfate anionic surfactants of the present invention include:

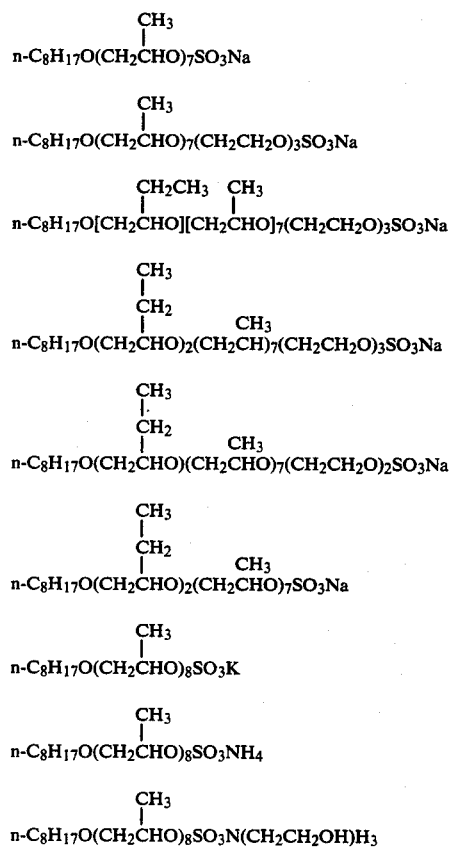

-continued

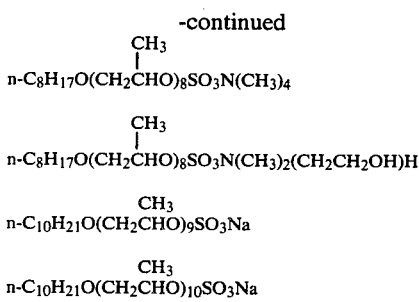

$$\text{n-C}_8\text{H}_{17}\text{O}(\text{CH}_2\overset{\overset{\displaystyle CH_3}{|}}{\text{CH}}\text{O})_8\text{SO}_3\text{N}(\text{CH}_3)_4$$

$$\text{n-C}_8\text{H}_{17}\text{O}(\text{CH}_2\overset{\overset{\displaystyle CH_3}{|}}{\text{CH}}\text{O})_8\text{SO}_3\text{N}(\text{CH}_3)_2(\text{CH}_2\text{CH}_2\text{OH})\text{H}$$

$$\text{n-C}_{10}\text{H}_{21}\text{O}(\text{CH}_2\overset{\overset{\displaystyle CH_3}{|}}{\text{CH}}\text{O})_9\text{SO}_3\text{Na}$$

$$\text{n-C}_{10}\text{H}_{21}\text{O}(\text{CH}_2\overset{\overset{\displaystyle CH_3}{|}}{\text{CH}}\text{O})_{10}\text{SO}_3\text{Na}$$

In accordance with the present invention, liquid low foaming alkoxylated ether sulfate anionic surfactant compositions based on linear chain alcohols having superior detergency characteristics for textile materials and fabric softening properties are provided. In addition, the anionic surfactant compositions of the present invention have been found to exhibit important advantages as detergent intermediates compared to alkoxylated anionic surfactant compositions produced from ethylene oxide alone. Hence, it has been found that the physical properties of the alkoxylated ether sulfates of the invention contrast with properties of commercially available ethoxylated ether sulfates derived from "detergent" or fatty range alcohols, which are solids at concentration of greater than about 60% whereas the alkoxylated ether sulfate surfactants of the invention are liquids at concentrations of 85% or greater. In addition, the ethoxylated ether sulfates derived from fatty alcohols require a solvent, e.g. 10 weight percent ethanol, in order to maintain a solution even at the 60 weight percent concentration; in contrast, no solvent except water is required to dissolve or stabilize the alkoxylated ether sulfate surfactants of the invention. The alkoxylated ether sulfate surfactants of the present invention will also avoid a gel phase upon dilution with water. This difference in physical properties between these surfactants provides a significant economic advantage associated with shipping and storage. In addition the alkoxylated ether sulfate of the invention can be spray dried without pluming and without the flammability problems associated with using ethanol in ethoxylated anionic surfactant formulations.

Furthermore, the alkoxylated branched chain alcohol ether sulfates of the invention are equivalent to or better as detergents than commercially employed surfactant compositions, for example dodecylbenzene sulfonate compositions, non-ionic surfactants, and commercially available ethoxylated ether sulfates, such as Neodol ® 253S. Moreover, alkoxylated ether sulfate surfactants of the invention are substantive to cotton and are employable as wash cycle fabric softeners; results obtained are comparable with those obtained using commercially available wash cycle fabric softening formulations.

Moreover, the alkoxylated ether sulfate surfactants of the present invention are stable and exhibit good detergency at hard water hardness of 500 ppm or higher and also have been shown to be exceptional lime soap dispersants, as compared with commercially available dodecylbenzene sulfonate compositions. Other advantages characteristic of the surfactant compositions of the present invention include good primary biodegradability, excellent solubility and good detergency in both hot and cold water, excellent solubility in organic solvents such as toluene, hexane, and 1,1,1-trichloroethane, non-corrosion to mild steel and most polymers, ability to be spray dried without volatility loss, good alkaline stability, and excellent compatibility with non-ionic and other surfactants in detergent formulations. The alkoxylated ether sulfate surfactants of the present invention, while being anionic surfactants, have many of the desirable properties of a nonionic surfactant.

The concentrated aqueous surfactant compositions of the invention comprise at least about 5%, but no more than about 50%, generally not more than about 40% by weight of water and an alkoxylated ether sulfate anionic surfactant conforming to Formula I above. In accordance with the present invention, it has been further found that aqeuous solutions of the alkoxylated ether sulfate anionic surfactant present in a wide range of "active concentrations" may be prepared; these solutions exhibit viscosity and dilution properties that enable them to be prepared as concentrates and diluted with water when preparing a detergent formulation containing "active concentration" of surfactant conventionally employed in such formulations, without detracting from the properties of such formulations, i.e. are readily diluted with water to any required or desired concentration without forming gels or lumps and are reasonably free-flowing. Hence, such solutions are, in general, characterized by having a viscosity, at 25° C., of less than 1000 cps, and preferably, of less than about 100 cps. As used herein, the term "active concentration" is used to denote the total concentration of "active" i.e. surface active, ingredients in the aqueous anionic surfactant composition.

The surfactant compositions of the invention may be prepared by known methods, for example, by alkoxylation of the linear chain alcohol, i.e., alcohol containing from 4 to 10 carbon atoms in the chain of which substantial quantities i.e. about 95% or greater are primary. Alkoxylation of the alcohol is effected at elevated temperatures, generally between about 70° and 150° C., preferably between about 90° and 100° C. at pressures ranging from atmospheric to about 500 psig, preferably between about 50 and 100 psig, in the presence of an alkaline catalyst, such as an alkali metal hydroxide, illustratively, potassium hydroxide, present in a concentration ranging from between about 0.01 and 1 weight percent preferably between about 0.2 and 0.3 weight percent of the reactant. In general, a controlled amount of propylene oxide or 1,2-butylene oxide, or an admixture thereof, is slowly contacted with the alcohol reactant, which optionally may be preheated to a liquid state, over a reaction time, generally ranging up to about 20 hours, in an amount sufficient to form the desired oxyalkylated reaction product mixture.

In general, sufficient alkylene oxide is employed in the alkoxylation reaction to effect preparation of an alkoxylated derivative having an average number of alkylene oxide units per molecule in the surfactant product of between 7 and 12, and preferably between 8 and 10. Optionally, if desired, in a second step, as is known in the art, for example, from Martin J. Schick, "Non-ionic Surfactants", pp. 118, Marcel Dekker, Inc., New York (1966) ethylene oxide may be added to the reaction product of the first alkoxylation step to produce an ethylene oxide "tipped" product having a primary hydroxyl group, or alternatively, this second alkoxylation step may be effected by use of a mixture of ethylene oxide and propylene oxide or 1,2 butylene oxide, thereby producing an alkoxylated ether characterized by a block or random structure, under the reaction conditions specified above for the first alkoxylation reaction. In general, when ethylene oxide alone is added, approximately one to four moles of ethylene oxide is added, and when a mixture of ethylene oxide and propylene oxide or 1,2-butylene oxide is employed, the molar ratio of ethylene oxide to such higher alkylene oxide range from about 1:1, preferably from about 2:1 to about 5:1. The amount of oxides employed when the second alkoxylation is performed is such that the resultant product contains a total molar ratio of oxyethylene groups to oxypropylene or oxybutylene groups from about 1:1 to about 1:10, and preferably from about 1:2 to about 1:4.

If desired, the oxyalkylation of the alcohol may be carried out in a suitable solvent, illustratively, an aromatic hydrocarbon such as toluene, benzene, ethers such as tetrahydrofuran and the like. Other solvents employable for this purpose include aliphatic hydrocarbons containing from about 5 to 12 carbon atoms, such as heptane, hexane octane and the like, thereby obviating the toxic associations connected with use of aromatic hydrocarbon solvents, if employed. It is also necessary to ensure that the alcohol reactant is free of water, and hence, vacuum stripping of the starting material may be employed in conventional manner.

Alcohols which may be employed in the preparation of the alkoxylated intermediates in production of the surfactant compositions of the present invention are commercially available and may be obtained, for example, by the Ziegler process, as disclosed in F. Asinger, "Mono-Olefin Chemistry and Technology" Pergamon Press, NY (1968); hence, suitable alcohols include any primary, linear plasticizer range alcohol containing of from about 4 to 10, preferably 8 to 10 carbon atoms in the chain. Illustrative suitable alcohols include n-butanol; n-hexanol; n-octanol; and n-decanol.

The alkoxylated alcohols obtained are converted to the sulfates typically by reaction with chlorosulfonic acid, sulfur trioxide, or concentrated sulfuric acid in accordance with well known procedures such as disclosed in U.S. Pat. Nos. 2,187,244 and 3,931,271. In general, for example, when sulfation is effected by use of chlorosulfonic acid, a slight excess of chlorosulfonic acid diluted with equal portion volumes of a solvent such as methylene chloride, is slowly added to a solution of oxyalkylated oligomer, present in equal volume portion, in methylene chloride over a period of 2 hours. The temperature is held at 10° to 25° C. using an icebath and nitrogen sweep. Sulfation with chlorosulfonic acid in the absence of solvent is also possible if good control over heat transfer is maintained.

The surfactant compositions of the invention are of high quality characterized as being essentially free of unpleasant odor. This is a significant advantage as compared with those alkoxylated surfactant compositions produced from Ziegler type alcohols which have been alkoxylated solely by ethylene oxide. It has been reported that such compositions derived from Ziegler alcohols exhibit a high and objectionable odor level.

According to the invention it is not necessary to separate the individual alkylene oxide ether alcohols by distillation or other separation techniques in order to accomplish the objectives of the invention. The entire reaction mixture which will contain an average number of alkylene oxide units selected from propylene oxide or 1,2-butylene oxide, present in an average number of between about 7 and 12, or optionally, in addition thereto a random mixture of such oxyalkylene groups with oxyethylene groups, may be directly sulfated to provide an anionic surfactant product with improved solubility, exhibiting the physical and chemical properties referred to hereinabove.

Following sulfation, the alkoxylated ether sulfate composition corresponding to Formula I, above, wherein M is hydrogen, is neutralized by known methods, for example, by reaction with: an alkali metal hydroxide, such as sodium hydroxide, as the most preferred, potassium hydroxide, lithium hydroxide; and alkaline earth metal hydroxide such as magnesium hydroxide, calcium hydroxide, cesium hydroxide, rubidium hydroxide, or aluminum hydroxide; ammonia or a substituted amine derivative thereof. Typical substituted amine derivative reactants employable for this purpose include ammonia, triethanolamine, triisopropanolamine and the like. Normally the neutralization agent is employed in concentration ranging from between about 25 and 50 weight percent to produce a product with a pH of between about 7 and 10, preferably between 7 and 7.7. If desired, a solvent such as a lower alkanol, illustratively ethanol or isopropanol in a concentration of at least 10%, when employed, may be used.

The following examples will serve to illustrate the practice of the invention, but they are not intended to limit it to the details described herein. Parts and percentages are by weight, temperatures are in degrees Centigrade, unless otherwise specified.

EXAMPLES

A. Preparation of alkoxylated derivative of appropriate alcohol

All reactions were carried out in a 2-gallon oil heated stirred stainless steel autoclave. A 0.25 percent catalyst solution was prepared using the appropriate "plasticizer" Ziegler alcohol and potassium hydroxide by preheating at 75°–100°. Water was removed under vacuum and the catalyst solution was charged hot under dry nitrogen into the autoclave. The remaining alcohol was added to the reactor followed by purging with dry nitrogen. The reactor was heated to 95° and dry alkylene oxide in the appropriate stoichiometry was slowly added over a period of 24–48 hours using a pressure demand control valve system to control the addition rate. A reference pressure was set at 60 psig, and if the reactor pressure dropped below this pressure the control valve opened and more alkylene oxide was charged to the reactor. When the pressure increased to greater than 60 psig, the valve closed. The alkylene oxide was contained in a hoke that was suspended on a weight load cell, thereby permitting the charging of the correct amount of alkylene oxide. Since the hoke had a 80 psig nitrogen pressure head, the overall reactor pressure increased to 80 psig when all the liquid alkylene oxide was pushed out of the load cell hoke into the reactor. When the reaction was complete, the product was removed hot from the reactor and was treated with Magnesol ® (4 grams per 250 grams of product) for 2 hours at 120° in order to remove the catalyst. The resulting product was vacuum filtered through a Cellite bed at 60°–80° to provide the pure oligomeric polyol. Hydroxyl number, VPO molecular weight, GPC analysis, and $^{13}C$ NMR were primarily used to characterize the product oligomers.

B. Preparation of Sulfate as a Derivative

1. Sulfation with Chlorosulfonic Acid and Neutralization

A slight excess of chlorosulfonic acid diluted 50/50 with methylene chloride was slowly added to a solution of oxyalkylated oligomer (50/50) in methylene chloride over the course of two hours. The temperature was held at 10°–25° using an ice-bath and a nitrogen sweep (approximately 2–5 liters/minute) was used to remove hydrochloric acid from the reaction zone. After the addition was complete, the mixture was allowed to stir an additional 1–2 hours at 35°–40°. The excess methylene chloride solvent was stripped from the sulfated product via rotary evaporation prior to neutralization. The product was neutralized with 50 percent sodium hydroxide to a pH of 7.5–9.0, and the neutralized product was cooled overnight at 10° C. and filtered to remove sodium chloride and sodium sulfate. The product was extracted with petroleum ether to remove unreacted oligomer and was stripped to remove water and any remaining solvent. Both of the above purification steps (i.e., filtration and extraction) are optional and need not be always used. The final alkoxylated ether sulfate anionic surfactant product is a liquid at active concentration of 90 wt. % or greater.

2. Sulfation with Sulfur Trioxide and Neutralization

Liquid sulfur trioxide diluted with an air stream was slowly added over a two hour period at 25° in an amount sufficient to provide 65% propoxylated oligomer conversion to the appropriate alkoxylated, e.g. propoxylated polyol in methylene chloride solvent. By holding the conversion low, acid build up and unsaturation due to elimination could be prevented. The sulfur trioxide incorporated into the $SO_3Na$ containing surfactant was determined by titration with Hyamine ®-1622 (to methylene blue end-point) and the unreacted sulfur trioxide was determined by scrubbing through sodium hydroxide followed by simple acid-base titration. At the end of the sulfation run, the temperature was increased to 35° for one hour and air was bubbled through the solution to ensure that all the unreacted sulfur trioxide was removed or reacted. The product was neutralized with 50 percent sodium hydroxide to a pH of 8.0 followed by extraction with petroleum ether to recover the unreacted propoxylated polyol for recycle.

EXAMPLES 1–7

A number of surfactants of the invention were prepared using the synthetic procedures outlined in paragraphs A and B-1 above. Their properties are set forth in Table I below.

TABLE I

Properties of Alkoxylated Alcohol Sodium Sulfates

| Example No. | Alcohol | Alkylene Oxide/ Units | Surface Tension[2] (Dynes/cm) | Draves Wetting[3] (Sec) | Ross Miles Foaming (cm)[4] Initial | Ross Miles Foaming (cm)[4] 5 Minutes | Detergency[5] Polyester % SR | Detergency[5] Polyester % D |
|---|---|---|---|---|---|---|---|---|
| 1 | N—Octanol | Propylene oxide/8 | 34.2 | 31.0 | 15.9 | 1.8 | 75.0 | 68.3 |
| 2 | N—heptanol | Propylene oxide/5 | 39.2 | 29.2 | 18.7 | 61 | 53.1 | 50.1 |
| 3 | N—Octanol | Propylene oxide/4 | 37.2 | 360.0 | 20.0 | 0.5 | 50.4 | 39.7 |
| 4 | N—Octanol | Propylene oxide/5 | 38.1 | 210.0 | 20.1 | 1.2 | 66.2 | 41.9 |
| 5 | Neodol ® 25[1] | Ethylene oxide/3 | 34.2 | 18.0 | 20.0 | 18.7 | 58.7 | 55.6 |
| 6 | Neodol ® 25[1] | Propylene oxide/3 | 33.2 | 17.4 | 18.4 | 15.7 | 47.5 | 45.1 |
| 7 | Neodol ® 25[1] | Propylene oxide/5 | 33.7 | 18.3 | 18.8 | 15.1 | 46.9 | 44.8 |

Notes:
[1] Neodol ® 25 = Shell $C_{12-15}$ fatty alcohol
[2] Measured on a 1% solution at 25° C.; Kraft Points is 1°.
[3] Draves wetting is measured on a 0.1 wt % solution at room temperature (77° F.)
[4] ASTM D1173-53 was used.
[5] Terg-o-tometer test with: Speed = 125 rpms; Temperature = 120° F.; Time = 10 minutes/ Surfactant concentration = .15 wt %; hardness = 150 ppm; 4" × 6" cloth - each wash batch used 5 soiled and 3 clean polyester fabric; the panels used in determining evaluation were coated with standard pad applied airborne/dust sebum soil.

$$\% \text{ Soil Removal (SR)} = \frac{R_L \text{ Soil BW} \times 100}{R_L \text{ Unsoiled} - R_L \text{ Soil BW}}$$

$$\% \text{ Detergency (D)} = \frac{R_L \text{ Soil AW} - (R_L \text{ Redeposition BW} - AW) \times 100}{R_L \text{ Redeposition} - R_L \text{ Soil BW}}$$

$R_L$ = Reflectance (L Scale)
AW = After Wash
BW = Before Wash

The results set forth in Table I comparing a typical surfactant of the present invention (Example 1) with a commercially available surfactant (Example 5), as well as with a number of surfactants which have been ethoxylated or propoxylated to a lesser degree than that of the composition of Example 1, demonstrate the obtainment of improved results of the compositions of the present invention with regard to surface activity, wetting, foaming and as a detergent with respect to polyester fabric.

EXAMPLES 8–11

The experimental procedure outlined under Examples No. 1–7 was followed to prepare alkoxylated anionic derivatives from the alcohols and alkylene oxide indicated in Table II below; the detergency results, obtained in the same manner as in Table I, above, employing water of the hardness indicated, are set forth in Table II, below.

TABLE II
Effect Water Hardness

| Example No. | Alcohol | Alkylene Oxide (Units) | (PPM) Hardness | Detergency Polyester % SR | Detergency Polyester % D |
|---|---|---|---|---|---|
| 8 | Neodol ® 25 | ethylene oxide[3] | 150 | 58.7 | 55.6 |
| 9 | Neodol ® 25 | ethylene oxide[3] | 500 | 49.1 | 47.3 |
| 10 | N—Octanol | propylene oxide[8] | 150 | 75.0 | 68.3 |
| 11 | N—Octanol | propylene oxide[8] | 500 | 75.5 | 69.4 |

The results set forth above in Table II show that water hardness has little or no effect on the propoxylated ether sulfate detergency characteristics of the invention and were comparable to those achieved by commercially available detergents.

EXAMPLES 12–17

The experimental procedure outlined under Example 1 was followed to prepare alkoxylated derivatives of the invention, while varying the base employed for neutralization; to demonstrate the counter-ion effect upon surface active properties; the detergency was obtained in the same manner as in Table I, above. The results are set forth in Table III, below.

TABLE III

| Example No. | Alcohol[R] | Alkylene Oxide/Units | Counter-Ion(M+) | Detergency Polyester % SR | Detergency Polyester % D |
|---|---|---|---|---|---|
| 12 | N—Octanol | propylene oxide/8 | Na | 75.0 | 68.3 |
| 13 | N—Octanol | propylene oxide/8 | $NH_4$ | 80.5 | 77.8 |
| 14 | N—Octanol | propylene oxide/8 | K | 76.8 | 69.9 |
| 15 | N—Octanol | propylene oxide/8 | $NH_3CH_2CH_2OH$ | 77.1 | 69.5 |
| 16 | N—Octanol | propylene oxide/8 | $NH_3CH_2CH(CH_3)OH$ | 81.3 | 78.7 |
| 17 | Neodol 25 | ethylene oxide/3 | Na | 58.7 | 55.6 |

It can thus be seen that valuable and highly desirable alkoxylated ether sulfate anionic surfactants which exhibit excellent detergency, high activity, good wetting, low foaming and fabric softening properties have been provided.

Although the alkoxylated ether sulfate anionic surfactants described in the foregoing have useful detergent properties per se, it is generally preferred to use them in combination with other detergent active compounds and with various adjuvants such as hydrotopes, typically cumene, xylene, and toluene sulfonates, perfumes, pH modifiers, inorganic salts, bacteriastats, dyes, solvents such as alkanols and carbitols, typically ethanol, isopropanol, methyl carbitol and ethyl carbitol and the like. Further, if desired, the surfactant compositions of the invention may be employed with other adjuvants specific to desired applications such as carboxymethyl cellulose, optical brighteners, corrosion inhibitors, alkaline builders, and the like, as is well known in the art.

Our invention has been described and illustrated by reference to specific embodiments thereof, and the examples illustrate the best mode presently known for carrying out the invention. It should be noted, however, that variations of these procedures are feasible and many such variations would be obvious to those skilled in the art in view of the disclosures contained herein.

We claim:

1. A water-soluble, liquid alkoxylated ether sulfate anionic surfactant having the formula:

$$R[OCH_2CH(R')]_mZnSO_3M$$

wherein R is a primary hydrocarbon linear alkyl radical containing of from about 4 to 10 carbon atoms; R' is a member selected from the group consisting of methyl and ethyl; m is an integer of from 7 to 12; Z is an oxyethylene group or a random mixture of oxyethylene groups and oxyalkylene groups present in the radical $[CH_2CH(R')O]$, the molar ratio of oxyethylene to oxyalkylene groups in said mixture being such that the total molar ratio of oxyethylene to oxyalkylene groups in said formula is from about 1:1 to 1:10; n is an integer of from 0 to 4; and M is hydrogen, an alkali metal, an alkaline earth metal; ammonium or a primary, secondary, tertiary or quaternary alkyl ammonium or alkylolammonium ion.

2. The anionic surfactant of claim 1 wherein R is an alkyl radical containing of from 8 to 10 carbon atoms.

3. The anionic surfactant of claim 1 wherein R' is methyl.

4. The anionic surfactant of claim 1 wherein R is an alkyl radical containing of from 8 to 10 carbon atoms and R' is methyl.

5. The anionic surfactant of claim 4 wherein M is an alkali metal.

6. The anionic surfactant of claim 4 wherein M is sodium.

7. The anionic surfactant of claim 4 wherein M is potassium.

8. The anionic surfactant of claim 4 wherein M is ammonium.

9. The anionic surfactant of claim 4 wherein M is hydrogen.

10. The anionic surfactant of claim 3 wherein m is an integer of from 8 to 10; n is 0 and M is sodium.

11. An aqueous, liquid surfactant concentrate composition comprising at least about 5%, but not more than 50%, by weight, of water, and the active anionic surfactant of claim 1.

12. An aqueous, liquid surfactant concentrate composition comprising at least about 5%, but not more than 50%, by weight, of water, and the active anionic surfactant of claim 4.

13. An aqueous, liquid surfactant concentrate composition comprising at least about 5%, but not more than 50%, by weight, of water, and the active anionic surfactant of claim 6.

14. An aqueous, liquid surfactant concentrate composition comprising at least about 5%, but not more than 50%, by weight, of water, and the active anionic surfactant of claim 10.

* * * * *